US00PP12773P2

(12) United States Plant Patent
Vandenberg

(10) Patent No.: US PP12,773 P2
(45) Date of Patent: Jul. 16, 2002

(54) CHRYSANTHEMUM PLANT NAMED 'SPICY NEW YOORLEANS'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 32 days.

(21) Appl. No.: 09/594,763

(22) Filed: Jun. 16, 2000

(51) Int. Cl.[7] ..... A01H 5/00
(52) U.S. Cl. ..... Plt./286
(58) Field of Search ..... Plt./286, 295, 298

(56) References Cited

U.S. PATENT DOCUMENTS 4,616,099 A * 10/1986 Sparkes ..... 47/58

OTHER PUBLICATIONS

Shukla, et al., 1993, "Mutation studies on early and late varieties of garden chrysanthemums", J. Nuclear Agric Biol., 22(3–4):138–142.*
Broertjes, et al., 1980, "A mutant of a mutant of a . . . Irradiation of progressive radiation induced mutants in a mutation breeding programme with *Chrysanthemum morifolium*", Euphytica 29:525–530.*
Gosling, ed., 1979, "The Chrysanthemum Manual—6$^{th}$ edition", The National Chrysanthemum Society, London, Essex Telegraph Press, Ltd., pp. 329–336.*
Broertjes, et al., 1978, "Application of Mutation Breeding Methods in the Improvement of Vegetatively Propagated Crops", Elsevier Sci. Pub. Co., New York, pp. 162–175.*
Searle, et al., 1968, "Chrysanthemums the Year Round", Blanford Press, London, pp. 27–29, 320–327.*
Chan, 1966, "Chrysanthemum and rose mutations induced by x–rays", Am. Soc. Hort. Sci. Proc., pp. 613–620.*
Broertjes, 1966, "Mutation breeding of chrysanthemums", Euphytica, 15:156–162.*
Dowrick, et al., 1966, "The induction of mutations in chrysanthemum using x– and gamma radiation", Euphytica, 15:204–210.*
UPOV–ROM, 2001/03, Plant Variety Database, GTI Jouve Retrieval Software, citation for 'Spicy New Yoorleans'.*
* cited by examiner

*Primary Examiner*—Howard J. Locker
(74) *Attorney, Agent, or Firm*—C. A. Whealy

(57) ABSTRACT

A distinct cultivar of Chrysanthemum plant named 'Spicy New Yoorleans', characterized by its upright and uniformly mounded plant habit; freely branching habit; uniform flowering response; early flowering, eight-week response time; freely flowering habit; daisy-type inflorescences that are about 6.5 cm in diameter; bright red and yellow bicolored ray florets and bright yellow disc florets; lack of pollen production; and good postproduction longevity with inflorescences maintaining good substance and color for about three weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Spicy New Yoorleans.

The new Chrysanthemum is a product of a mutation induction breeding program conducted by the Inventor in Fort Myers, Fla., and Salinas, Calif. The objective of the program is to create new Chrysanthemum cultivars with desirable inflorescence form and floret colors and good postproduction longevity.

The new Chrysanthemum originated by exposing unrooted cuttings of the Chrysanthemum cultivar New Yoorleans, disclosed in U.S. Plant Pat. No. 11,215, to X-ray radiation in December, 1996, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemum was discovered and selected by the Inventor as a single flowering plant within this population in April, 1997. The selection of this plant was based on its desirable inflorescence form and ray floret color.

Asexual reproduction of the new Chrysanthemum by vegetative tip cuttings was first conducted in Salinas, Calif. in July, 1997. Asexual reproduction by cuttings has shown that the unique features of this new Chrysanthemum are stable and reproduced true to type in successive generations.

SUMMARY OF THE INVENTION

The cultivar Spicy New Yoorleans has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Spicy New Yoorleans'. These characteristics in combination distinguish 'Spicy New Yoorleans' as a new and distinct Chrysanthemum:

1. Upright and uniformly mounded plant habit.
2. Freely branching, dense and full plants.
3. Uniform flowering response.
4. Early flowering, eight-week response time.
5. Freely flowering.
6. Daisy-type inflorescences that are about 6.5 cm in diameter.

7. Bright red and yellow bicolored ray florets and bright yellow disc florets.
8. Production of pollen has not been observed.
9. Good postproduction longevity with inflorescences maintaining good substance and color for about three weeks in an interior environment.

Plants of the new Chrysanthemum differ from the Chrysanthemum cultivar Festive New Yoorleans, disclosed in U.S. Plant patent application Ser. No. 09/525,660, primarily in ray floret color.

Plants of the new Chrysanthemum differ from plants of the parent Chrysanthemum cultivar New Yoorleans in the following characteristics:

1. Ray florets of plant of the new Chrysanthemum are red and yellow bicolored whereas ray florets of plants of the cultivar New Yoorleans are dark pink and white bicolored.
2. Plants of the new Chrysanthemum flower about one or two days later than plants of the cultivar New Yoorleans.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the sheet comprises a top perspective view of a typical flowering plant of 'Spicy New Yoorleans'.

The photograph at the bottom of the sheet comprises a close-up view of typical inflorescences of the cultivar Spicy New Yoorleans.

DETAILED BOTANICAL DESCRIPTION

In the following description, color references are made to The Royal Horticultural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as spray-types. Measurements and numerical values represent averages of typical flowering plants.

Botanical classification: *Dendranthema grandiflora* cultivar Spicy New Yoorleans.

Commercial classification: Daisy-type potted Chrysanthemum.

Parentage: Induced mutation of the Chrysanthemum cultivar New Yoorleans, disclosed in U.S. Plant Pat. No. 11,215.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous daisy-type potted Chrysanthemum which is typically grown as a spray-type. Inverted triangle; stems upright; uniformly mounded plant habit. Freely branching, about four lateral branches develop after removal of terminal apex (pinching); dense and full plants. Moderate to high vigor.

*Plant height.*—About 27 cm.

*Plant width.*—About 36 cm.

*Lateral branches.*—Length: About 19 cm. Diameter: About 4 mm. Internode length: About 1.4 cm. Strength: Strong, flexible. Texture: Pubescent. Color: 144A.

*Foliage description.*—Arrangement: Alternate. Length: About 5.8 cm. Width: About 4.7 cm. Apex: Cuspidate. Base: Mostly truncate. Margin: Palmately lobed, sinuses between lateral lobes parallel to divergent, occasionally overlapping. Texture: Upper and lower surfaces with very fine pubescence; veins prominent on lower surface. Color: Young foliage upper surface: 147A. Young foliage lower surface: 147B. Mature foliage upper surface: 147A. Mature foliage lower surface: 147B. Venation upper surface: 147A to 147B. Venation lower surface: 147B. Petiole length: About 1.5 cm. Petiole diameter: About 2.5 mm. Petiole color: 147A to 147B.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences maintain good color and substance for about three weeks in an interior environment.

*Quantity of inflorescences.*—Typically grown as a spray-type; freely flowering with about six inflorescences per lateral stem, about 24 inflorescences per plant.

*Inflorescence bud.*—Height: About 6 mm. Diameter: About 8 mm. Color: 147A.

*Inflorescence size.*—Diameter: About 6.5 cm. Depth (height): About 2.3 cm. Diameter of disc: About 1.5 cm. Receptacle diameter: About 5 mm.

*Ray florets.*—Shape: Elongated-oblong. Orientation: Somewhat upright, about 20 to 30° from perpendicular to peduncle. Aspect: Straight and somewhat concave. Length: About 3.1 cm. Width: About 1.1 cm. Apex: Mostly acute. Base: Attenuate; short corolla tube. Margin: Entire. Texture: Smooth, glabrous, satiny. Number of ray florets per inflorescence: About 22; about 2 rows. Color: When opening, upper surface: Red, 45A to 46A, and yellow, 9A to 7A, bicolored. Apex, mostly red; mid-section, yellow and red longitudinal stripes; base, yellow. When opening, lower surface: Ground color and base, yellow, 9B; faint longitudinal stripes mostly towards apex, red, close to 46A or 53A. Fully opened, upper surface: Red, 45A, 46A and/or 53A, and yellow, 9A, bicolored. Apex, mostly red; mid-section, yellow and red longitudinal stripes; base, yellow. Fully opened, lower surface: Ground color and base, yellow, 9B to 9C; faint longitudinal stripes mostly towards apex, red, close to 46A or 53A.

*Disc florets.*—Shape: Tubular, elongated. Apex: Five-pointed. Length: About 5 mm. Width: Apex, about 1.5 mm; base, about 1 mm. Number of disc florets per inflorescence: About 134. Color: Immature: 144A. Mature: Apex: 9A. Mid-section: 154D. Base: 155D.

*Peduncles.*—Length: First peduncle: About 4.3 cm. Fourth peduncle: About 7.2 cm. Diameter: About 2 mm. Angle to vertical: About 40 to 45° from vertical. Strength: Strong, flexible. Color: 144A.

*Reproductive organs.*—Androecium: Present on disc florets only. Anther color: 12A. Pollen amount: Not observed. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Spicy New Yoorleans', as illustrated and described.

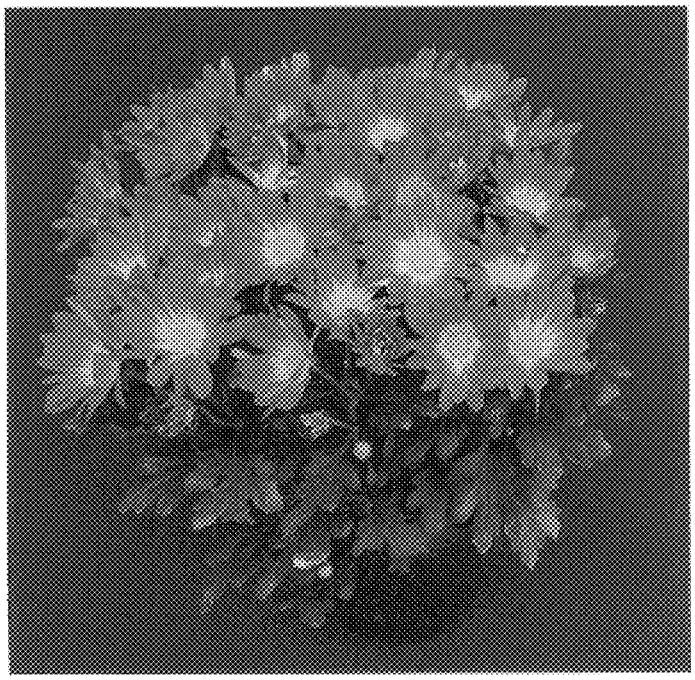
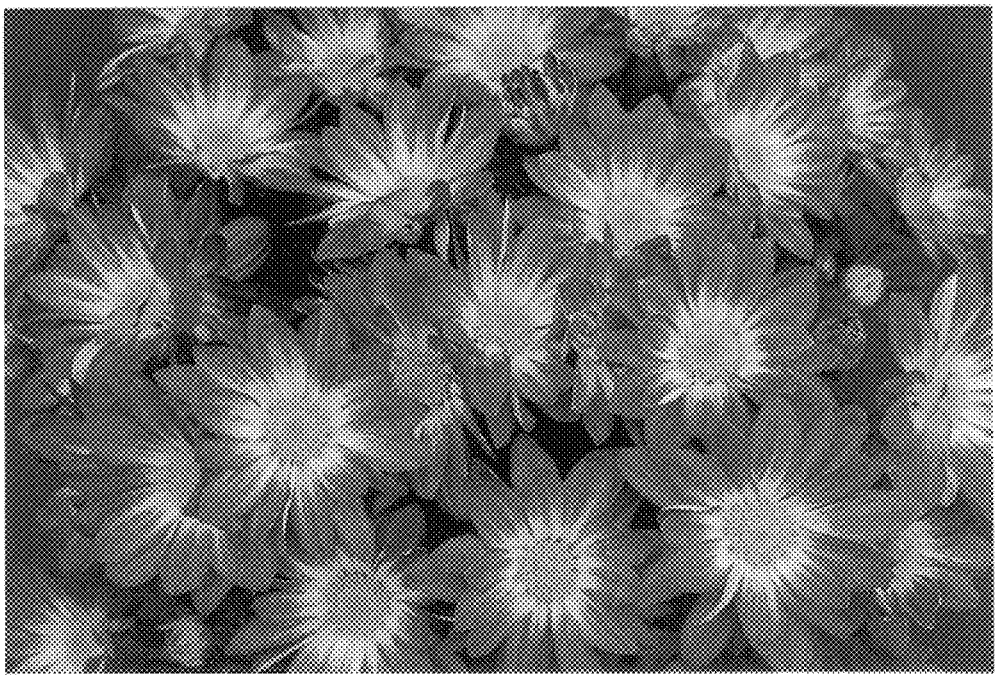

* * * * *